(12) United States Patent
Nauman et al.

(10) Patent No.: US 12,171,903 B2
(45) Date of Patent: Dec. 24, 2024

(54) BIORESORBABLE POROUS METALS FOR ORTHOPAEDIC APPLICATIONS

(71) Applicant: Purdue Research Foundation, West Lafayette, IN (US)

(72) Inventors: Eric Nauman, West Lafayette, IN (US); Lia Stanciu, West Lafayette, IN (US); Michael J. Heiden, West Lafayette, IN (US); Madhi Dehestani, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 821 days.

(21) Appl. No.: 17/157,949

(22) Filed: Jan. 25, 2021

(65) Prior Publication Data
US 2021/0145586 A1  May 20, 2021

Related U.S. Application Data

(62) Division of application No. 15/212,947, filed on Jul. 18, 2016, now Pat. No. 10,898,331.
(Continued)

(51) Int. Cl.
*A61L 27/04* (2006.01)
*A61F 2/28* (2006.01)
(Continued)

(52) U.S. Cl.
CPC .............. *A61L 27/042* (2013.01); *A61F 2/28* (2013.01); *A61L 27/047* (2013.01); *A61L 27/12* (2013.01);
(Continued)

(58) Field of Classification Search
CPC ...... C01G 53/50; C01G 53/006; C01G 53/42; C01G 53/44; C01G 53/04; C01G 53/00;
(Continued)

(56) References Cited

U.S. PATENT DOCUMENTS 8,790,402 B2    7/2014  Monaghan et al.
2006/0002810 A1 * 1/2006  Grohowski, Jr. ....... B22F 1/103
                                                        419/2
(Continued)

FOREIGN PATENT DOCUMENTS

WO   WO-2009032956 A1 *  3/2009  ........... A61L 27/306

OTHER PUBLICATIONS

Azo Materials; "Stainless Steel—Grade 17-4 (UNS S17400)", webpage: https://www.azom.com/article.aspx?ArticleID=6778; 2012, pp. 1-3 (Year: 2012).*
(Continued)

*Primary Examiner* — Adil A. Siddiqui
(74) *Attorney, Agent, or Firm* — Reichel Stohry Dean LLP; Natalie J. Dean

(57) ABSTRACT

Methods of producing bioresorbable porous biocomposites for orthopaedic applications are provided. In an exemplary embodiment of a resorbable orthopaedic implant of the present disclosure, the implant comprises a porous alloy of at least a first metal and a second metal sintered together, the alloy configured to resorb into a body at substantially an atomic level without flaking off, wherein a porosity of the implant is defined by a first plurality of interconnected holes having a first range of sizes.

20 Claims, 15 Drawing Sheets

Related U.S. Application Data

(60) Provisional application No. 62/193,776, filed on Jul. 17, 2015.

(51) Int. Cl.
| | |
|---|---|
| *A61F 2/30* | (2006.01) |
| *A61L 27/12* | (2006.01) |
| *A61L 27/56* | (2006.01) |
| *A61L 27/58* | (2006.01) |
| *B22F 3/11* | (2006.01) |
| *B22F 3/24* | (2006.01) |
| *B22F 5/10* | (2006.01) |
| *C22C 38/04* | (2006.01) |

(52) U.S. Cl.
CPC ............... *A61L 27/56* (2013.01); *A61L 27/58* (2013.01); *B22F 3/1121* (2013.01); *B22F 3/24* (2013.01); *A61F 2002/2817* (2013.01); *A61F 2002/30968* (2013.01); *A61F 2210/0004* (2013.01); *A61F 2250/0023* (2013.01); *B22F 5/10* (2013.01); *B22F 2998/10* (2013.01); *B22F 2999/00* (2013.01); *C22C 38/04* (2013.01)

(58) Field of Classification Search
CPC .... C01G 53/54; C01G 45/02; C01G 45/1242; C01G 51/04; C01G 45/00; C01G 53/66; C01G 49/00; C01G 49/0081; C01G 53/06; C01G 19/02; C01G 3/02; C01G 55/00; C01G 15/00; C01G 45/1228; C01G 49/06; C01G 51/54; C01G 53/40; C01G 1/02; C01G 23/08; C01G 25/00; C01G 25/02; C01G 31/02; C01G 45/006; C01G 49/02; C01G 51/50; C01G 55/004; C01G 1/00; C01G 23/053; C01G 23/0536; C01G 51/42; C01G 9/02; C01G 23/003; C01G 23/006; C01G 3/006; C01G 39/02; C01G 45/1257; C01G 49/0018; C01G 51/00; C01G 9/003; C01G 15/006; C01G 17/00; C01G 21/21; C01G 23/00; C01G 37/033; C01G 41/00; C01G 45/12; C01G 45/1214; C01G 45/1221; C01G 49/08; C01G 49/10; C01G 51/06; C01G 51/44; C01G 53/10; C01G 53/58; C01G 56/004; C01G 56/005; A61L 27/042; A61L 27/047; A61L 27/12; A61L 27/56; A61L 27/58; A61F 2/28; A61F 2002/2817; A61F 2002/30968; A61F 2210/0004; A61F 2250/0023; B22F 3/1121; B22F 3/24; B22F 5/10; B22F 2998/10; B22F 2999/00; C22C 38/04

USPC ........................................................ 423/138
See application file for complete search history.

(56) References Cited

U.S. PATENT DOCUMENTS

| | | |
|---|---|---|
| 2007/0296106 A1 | 12/2007 | Munz |
| 2011/0172798 A1 | 7/2011 | Staiger |
| 2014/0271768 A1 | 9/2014 | Radisch et al. |
| 2014/0348688 A1 | 11/2014 | Bal et al. |
| 2015/0076114 A1* | 3/2015 | Ciranni ............... A61L 27/047 216/104 |

OTHER PUBLICATIONS

Imola et al., Resorbable Plate Fixation in Pediatric Craniofacial Surgery, Arch Facial Plast Surg., Apr. 2001; 3: 79-90, Am Med Assoc, USA.

Laughlin et al., Resorbable Plates for the Fixation of Mandibular Fractures: A Prospective Study, J Oral Maxillofac Surg. 2007; 65: 89-96, Am Assoc of Oral and Maxillofacial Surgeons, USA.

Heiden et al., Magnesium, Iron and Zinc Alloys, the Trifecta of Bioresorbable Orthopaedic and Vascular Implantation—A Review, J Biotechnol Biomater, Apr. 30, 2015; 5(2); 178-186; DOI: 10.4172/2155-952X.1000178.

Prakasam et al., Biodegradable Materials and Metallic Implants - A Review, J Funct. Biomater., Sep. 26, 2017; 8(44); DOI: 10.3390/jfb8040044.

Hermawan, Hendra, Updates on the Research and Development of Absorbable Metals for Biomedical Applications, Progress in Biomater., May 22, 2018; 7:93-110; Springer, DOI: 10.1007/s40204-018-0091-4.

Santos et al., Chapter 10: Bioresorbable Metallic Implants: Surface Functionalization with Nanoparticles and Nanostructures, Advanced Materials and their Applications—Micro to nano scale, Jan. 2017, 219-241, One Central Press, USA.

Jain et al., Comparison of Tensile Strength of Resorbable Plating Systems Used in Monocortical Mandible Angle Osteotomy Repair, Arch Facial Plast Surg., Nov. 2006; 8: 390-395, Am Med Assoc, USA.

Pina and Ferreira, Bioresorbable Plates and Screws for Clinical Applications: A Review, J Healthcare Engineering 2012; 3(2): 243-260, USA.

Bohner, Marc, Resorbable biomaterials as bone graft substitutes, Mater. Today, Jan. 2010; 13(1-2): 26-30, Elsevier.

Heiden et al., Nanoporous metals for biodegradable implants: Initial bone mesenchymal stem cell adhesion and degradation behavior, Society for Biomaterials—Journal of Biomedical Research, Mar. 21, 2016, 1747-1758, USA.

Arifn et al., Material processing of hydorxyapatite and titanium alloy (HA/Ti) composite as implant materials using powder metallurgy: A Review, Materials and Design, 55 92014, 165-175, available online Sep. 25, 2013, Elsevier.

* cited by examiner

BIORESORBABLE POROUS METALS FOR ORTHOPAEDIC APPLICATIONS

PRIORITY

The present application is related to, a divisional application of, and claims the priority benefit of U.S. Nonprovisional patent application Ser. No. 15/212,947 to Nauman et al., filed Jul. 17, 2016, which issues as U.S. Pat. No. 10,898,331 on Jan. 26, 2021 and is related to and claims the priority benefit of U.S. Provisional Patent Application Ser. No. 62/193,776, filed Jul. 17, 2015. The contents of each of the foregoing applications are incorporated herein by reference in their entireties.

TECHNICAL FIELD

The present application relates to orthopaedic implants, and specifically to orthopaedic implants with bioresorbable materials.

BACKGROUND

This section introduces aspects that may help facilitate a better understanding of the disclosure. Accordingly, these statements are to be read in this light and are not to be understood as admissions about what is or is not prior art.

Currently, medical operations that require placement of a temporary orthopaedic implant to mechanically support bone-like structures during the body's natural healing process are typically followed-up with a second surgery to remove the implant. The additional surgery results in higher medical cost for patients and increases the risk of complications. Alternatively, the implant can be resorbed into the body. These implants include screws, pins, suture anchors, staples, etc. For the bioresorbable approach, the implants must have sufficient strength to fully support surrounding tissue during the natural healing period, provide biocompatibility without toxicity and inflammatory side effects, promote tissue generation on and about the implant, be compatible with magnetic environment, e.g., magnetic resonance imaging, and avoid release in the form of flaking of material beyond the body's natural systems ability to take up the released material. Iron-manganese (FeMn) alloys are known to be materials suitable for some of these requirements. However, given the current status of magnesium implants, promotion of tissue generation has been suboptimal due to the high speed at which the implants resorb.

Therefore, there is an unmet need for a novel approach that not only allows the implants to be resorbed into the subject's body, but also promotes vascularization and bone growth.

BRIEF SUMMARY

In an exemplary embodiment of a resorbable orthopaedic implant of the present disclosure, the implant comprises a porous alloy of at least a first metal and a second metal sintered together, the alloy configured to resorb into a body at substantially an atomic level without flaking off, wherein a porosity of the implant is defined by a first plurality of interconnected holes having a first range of sizes.

In an exemplary embodiment of a resorbable orthopaedic implant of the present disclosure, the first range of pore sizes is between about 200 μm to about 1000 μm.

In an exemplary embodiment of a resorbable orthopaedic implant of the present disclosure, the implant further comprises a second plurality of interconnected holes having a second range of sizes defined therein that is at least about one order of magnitude larger than the first range of sizes, the first plurality of holes being interconnected with the second plurality of holes.

In an exemplary embodiment of a resorbable orthopaedic implant of the present disclosure, the implant further comprises a second plurality of interconnected holes having a second range of sizes defined that is at least about one order of magnitude smaller than the first range of sizes, the first plurality of holes being interconnected with the second plurality of holes.

In an exemplary embodiment of a resorbable orthopaedic implant of the present disclosure, the porous alloy has a surface roughness at or between 2 nm and 5 μm.

In an exemplary embodiment of a resorbable orthopaedic implant of the present disclosure, the surface roughness is generated by a dealloying process.

In an exemplary embodiment of a resorbable orthopaedic implant of the present disclosure, the implant is further configured to include a bone growth agent impregnated into a predetermined percentage of the interconnected holes.

In an exemplary embodiment of a resorbable orthopaedic implant of the present disclosure, the implant further comprises a bone growth agent that is sintered together with the first metal and the second metal.

In an exemplary embodiment of a resorbable orthopaedic implant of the present disclosure, the bone growth agent is hydroxyapatite.

In an exemplary embodiment of a resorbable orthopaedic implant of the present disclosure, the first metal comprises manganese (Mn) and wherein the second metal comprises iron (Fe).

In an exemplary embodiment of a resorbable orthopaedic implant of the present disclosure, a ratio of Mn to Fe is at our about 25% Mn/75% Fe to at our about 40% Mn/60% Fe.

In an exemplary embodiment of a resorbable orthopaedic implant of the present disclosure, the plurality of the interconnected holes are generated by positioning salt particles with Mn and Fe and a bone growth agent before starting the Mn and the Fe are sintered together, wherein sizes of the salt particles correspond to the first range of sizes of the first plurality of interconnected holes.

In an exemplary embodiment of a resorbable orthopaedic implant of the present disclosure, a ratio of the salt particles to the porous alloy is up to 50% by weight.

In an exemplary embodiment of an implant of the present disclosure, the implant comprises a porous alloy comprising manganese (Mn), iron (Fe), and a bone growth material, the implant having a first plurality of interconnected holes defined therein, the implant configured to resorb into a body at substantially an atomic level without flaking off.

In an exemplary embodiment of an implant of the present disclosure, the implant has a surface roughness at or between 2 nm and 5 μm.

In an exemplary embodiment of a method for producing a resorbable orthopaedic implant of the present disclosure, the method comprises generating a complex by compacting a quantity of a first metal, a second metal, and salt particles having a first range of sizes; heating the complex to a first temperature below the melting point of the first metal, the second metal, and the salt particles; cooling the heated complex to a second temperature below the first temperature; and washing the cooled complex with a washing solution configured to wash away the salt particles so to generate a plurality of interconnected holes corresponding to the first range of sizes of the salt particles.

In an exemplary embodiment of a method for producing a resorbable orthopaedic implant of the present disclosure, the method further comprises the step of dealloying the complex using an acid to provide a surface roughness between 2 nm and 5 µm.

In an exemplary embodiment of a method for producing a resorbable orthopaedic implant of the present disclosure, the step of generating the complex is performed by compacting a bone growth agent with the first metal, the second metal, and the salt particles.

In an exemplary embodiment of a method for producing a resorbable orthopaedic implant of the present disclosure, the step of generating the complex comprises compacting the first metal comprising manganese (Mn), the second metal comprising iron (Fe), the salt particles comprising sodium chloride (NaCl), and the bone growth agent comprising hydroxyapatite (HA).

In an exemplary embodiment of a method for producing a resorbable orthopaedic implant of the present disclosure, the step of compacting is performed at or about 17,000 lbf, and wherein the step of heating is performed to heat the complex to or about 750° C.

In an exemplary embodiment of a method for producing a resorbable orthopaedic implant of the present disclosure, the first range of pore sizes is between about 200 µm to about 1000 µm.

In an exemplary embodiment of a method for producing a resorbable orthopaedic implant of the present disclosure, the salt particles further having a second range of sizes that is at least about one order of magnitude larger than the first range of size, the first plurality of holes being interconnected with the second plurality of holes.

In an exemplary embodiment of a method for producing a resorbable orthopaedic implant of the present disclosure, the method further comprises dealloying the complex to provide a surface roughness between 2 nm and 5 µm.

In an exemplary embodiment of a method for producing a resorbable orthopaedic implant of the present disclosure, the salt particles having a second range of sizes that is at least about one order of magnitude smaller than the first range of size, the first plurality of holes being interconnected with the second plurality of holes.

In an exemplary embodiment of a method for producing a resorbable orthopaedic implant of the present disclosure, the method further includes impregnating the complex with a bone growth agent.

In an exemplary embodiment of a method for producing a resorbable orthopaedic implant of the present disclosure, the bone growth agent is hydroxyapatite.

In an exemplary embodiment of a method for producing a resorbable orthopaedic implant of the present disclosure, the first and second metals are Fe and Mn.

In an exemplary embodiment of a method for producing a resorbable orthopaedic implant of the present disclosure, the ratio of Mn to that of the complex is between about 25% and 40%.

In an exemplary embodiment of a method for producing a resorbable orthopaedic implant of the present disclosure, the ratio of the salt to the first and second metals is up to 50%.

In an exemplary embodiment of a method for producing a resorbable orthopaedic implant of the present disclosure, the washing solution is water.

In an exemplary embodiment of a method for producing a resorbable orthopaedic implant of the present disclosure, the heating is accomplished by pressurizing the complex.

In an exemplary embodiment of a method for producing a resorbable orthopaedic implant of the present disclosure, the heating is accomplished by heating the complex.

In an exemplary embodiment of a method for producing a resorbable orthopaedic implant of the present disclosure, the heating is accomplished by a combination of heating and pressurizing the complex.

In an exemplary embodiment of a method for producing a resorbable orthopaedic implant of the present disclosure, the impregnation of the bone growth agent is by sintering the bone growth agent with the first and second metals.

BRIEF DESCRIPTION OF THE DRAWINGS

The disclosed embodiments and other features, advantages, and disclosures contained herein, and the matter of attaining them, will become apparent and the present disclosure will be better understood by reference to the following description of various exemplary embodiments of the present disclosure taken in conjunction with the accompanying drawings, wherein.

Figure 1:
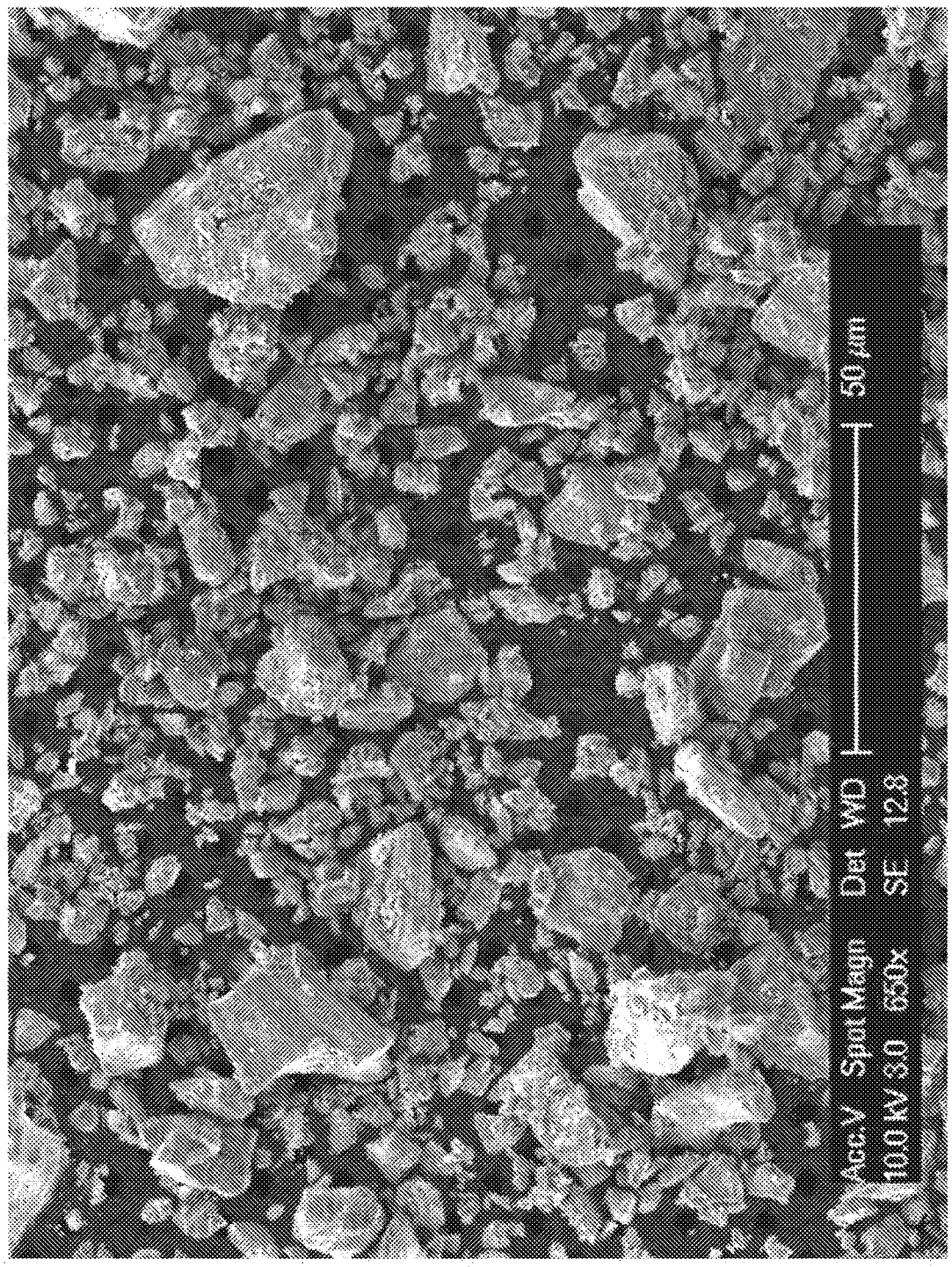
FIG. 1 is a scanning electron microscope (SEM) image of iron (Fe) powder with an average diameter of about 21 µm.

The attached drawings are for purposes of illustration and are not necessarily to scale.

An overview of the features, functions and/or configurations of the components depicted in the various figures will now be presented. It should be appreciated that not all of the features of the components of the figures are necessarily described. Some of these non-discussed features, such as various couplers, etc., as well as discussed features are inherent from the figures themselves. Other non-discussed features may be inherent in component geometry and/or configuration.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

A novel arrangement for implantable bioresorbable materials which can promote bone growth and vascularization is provided. The arrangement described herein is based on iron manganese alloys, however, other bioresorbable alloys known in the art can also benefit from the novel processing and arrangement described herein. The arrangement includes impregnation of a bone growth agent, e.g., hydroxyapatite, into the porous alloy to promote bone growth and vascularization while the implant is used temporarily during the body's natural healing process.

Figure 2:
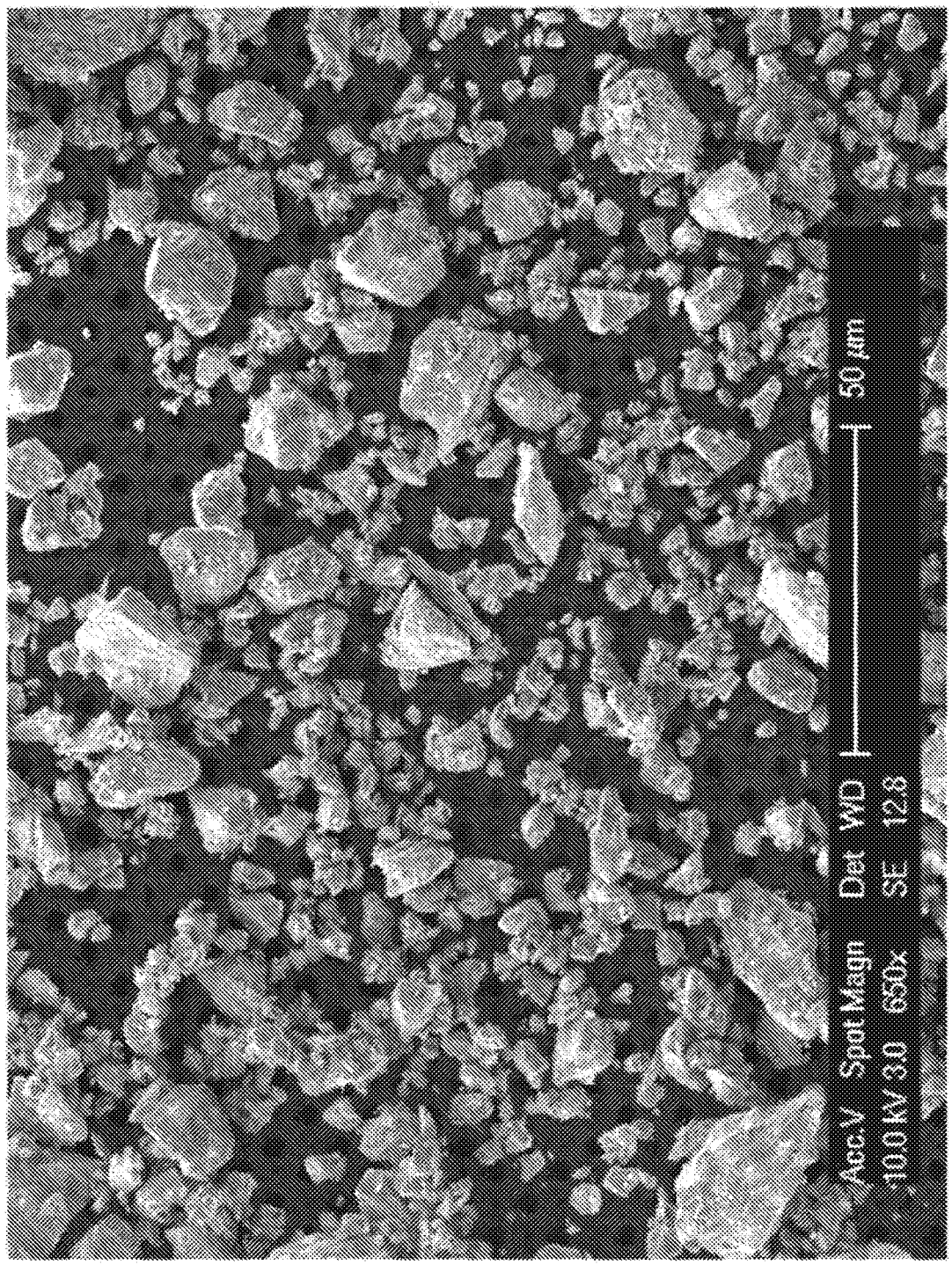
FIG. 2 is an SEM image of manganese (Mn) powder with an average diameter of about 24 µm.
Figure 3:
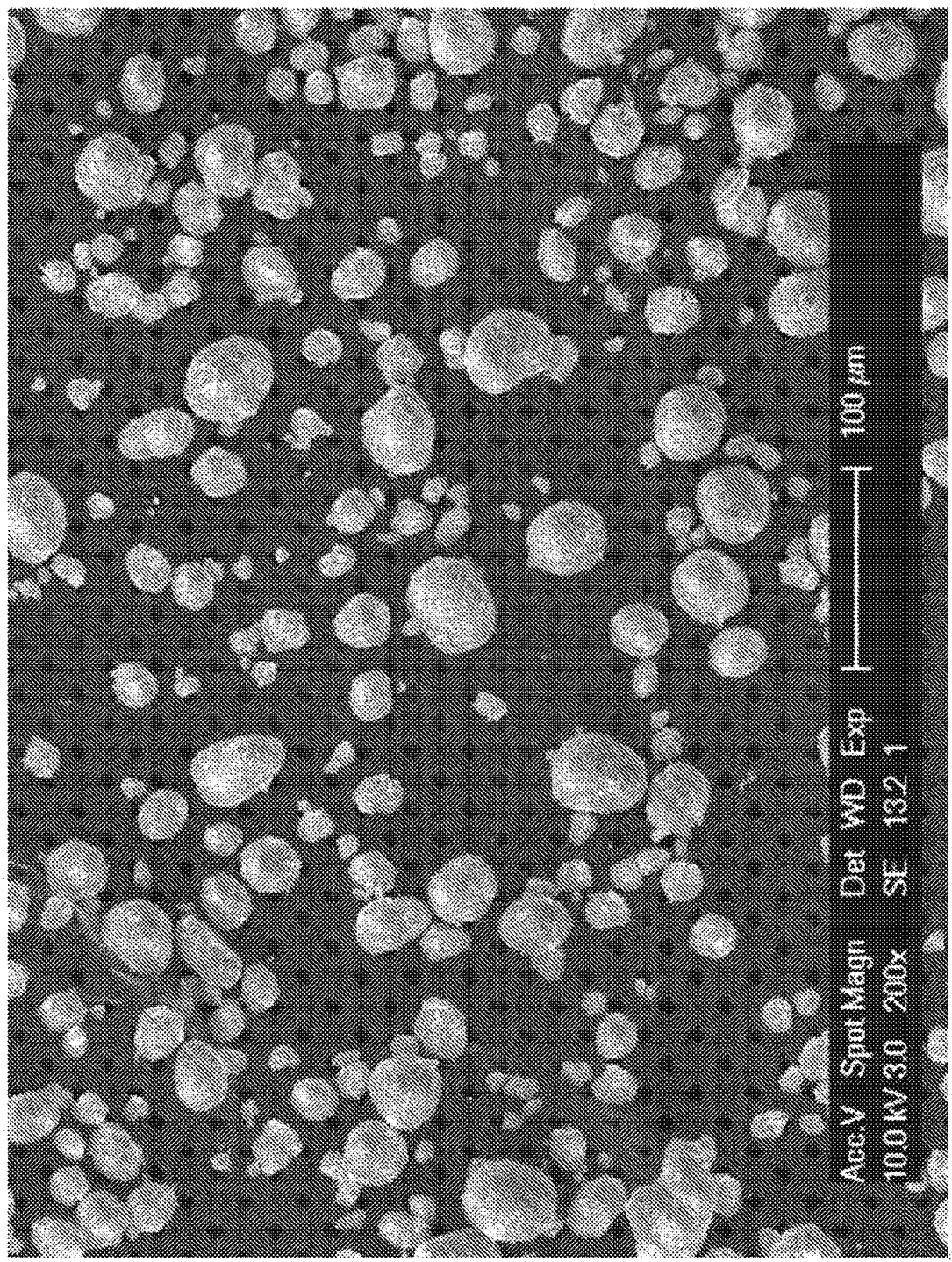
FIG. 3 is an SEM image of hydroxyapatite powder (HA) with an average diameter of about 24 µm.
Figure 4:
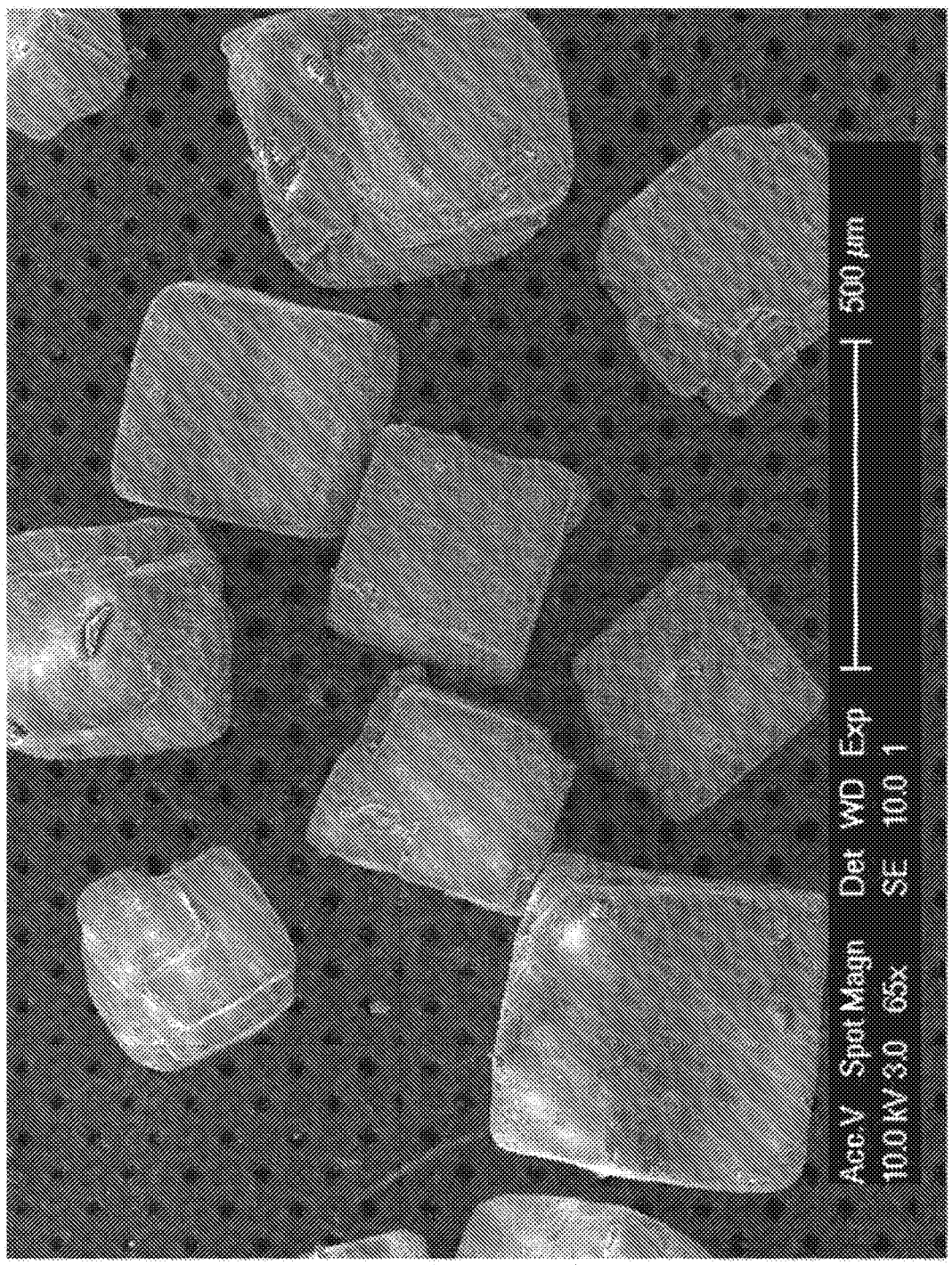
FIG. 4 is an SEM image of sodium chloride (NaCl) salt with an average diameter of about 282 µm±45 µm.

Referring to FIG. 1, a scanning electron microscope (SEM) image of iron (Fe) powder is shown, with an average diameter of about 21 μm depicted therein. The Fe powder comes in all sorts of sizes and shapes. Referring to FIG. 2, a SEM image of manganese (Mn) powder is shown, with an average diameter of about 24 μm depicted therein. The Mn powder also comes in all sorts of sizes and shapes. Referring to FIG. 3, an SEM image of hydroxyapatite (HA) powder is shown, with an average diameter of about 24 μm depicted therein. The HA powder also comes in all sorts of sizes and shapes. Next, FIG. 4 is an SEM image of sodium chloride (NaCl) salt with an average diameter of about 282 μm±45 μm.

Figure 5:
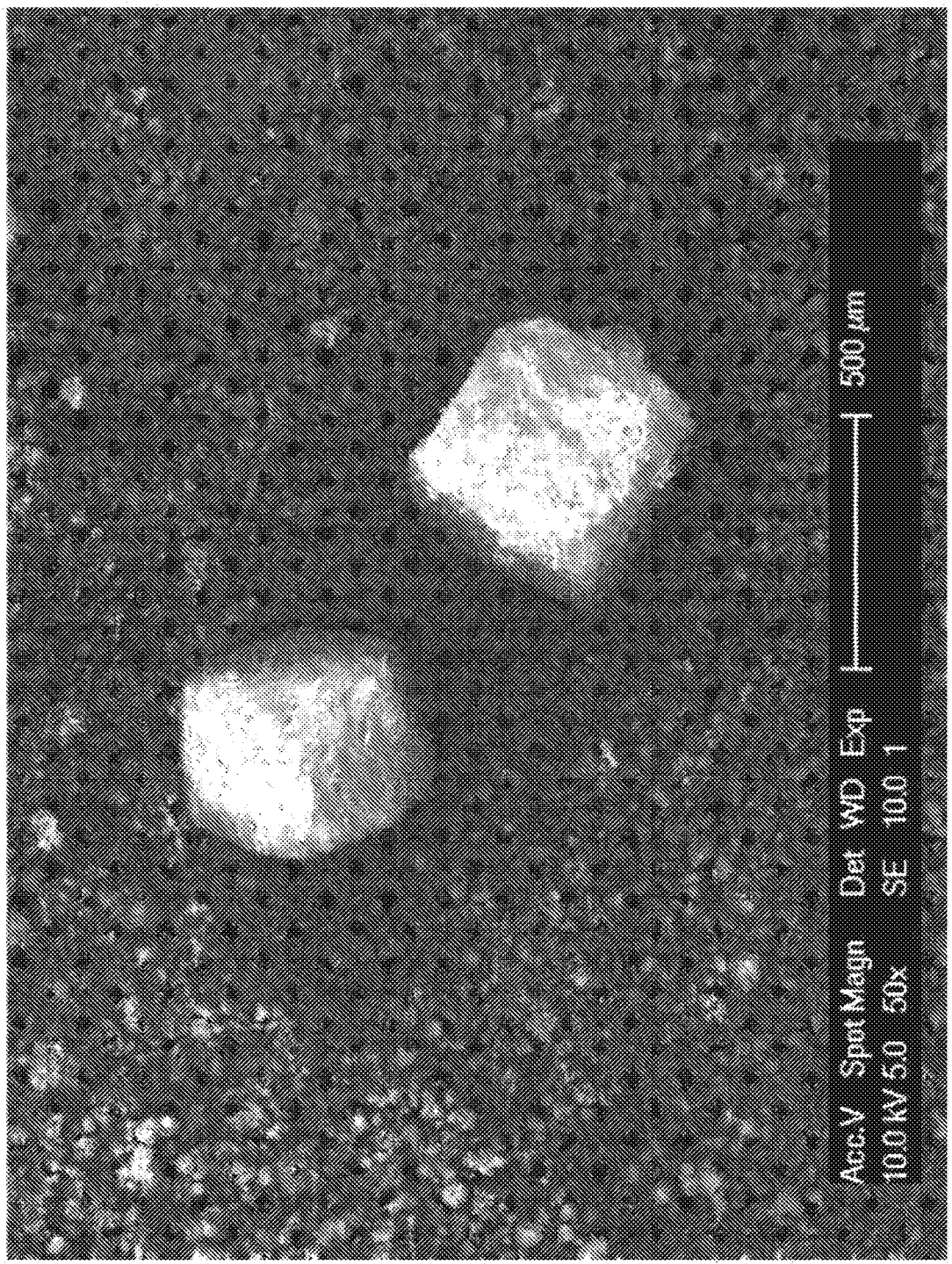
FIG. 5 is an SEM image of 40% Fe-30 Mn and 10% HA powder mixture with 50% NaCl mixed homogenously for 30 minutes, according to an exemplary embodiment of the present disclosure.

Referring to FIG. 5, an SEM image of a mixture of Fe, Mn, hydroxyapatite, and NaCl salt is shown, where by weight, the mixture of Fe to Mn is 70% Fe to 30% Mn, and which can range from 75% Fe to 60% Fe and 25% to 40% Mn; and by weight the mixture of NaCl to the mixture of Fe and Mn and HA is 50% NaCl and 40% Fe—Mn mixture and 10% HA. In various embodiments, the mixture of Fe to MN can range from at our about 60% Fe to 40% Mn, to or about 75% Fe to 25% Mn, by weight. In at least one embodiment, by weight, the mixture comprises at or about 50% NaCl, 40% Fe/Mn mixture, and 10% HA. The bone growth material HA can promote tissue development into and around the bioresorbable implant while the implant is being resorbed into the body during the natural healing process.

Figure 6A:
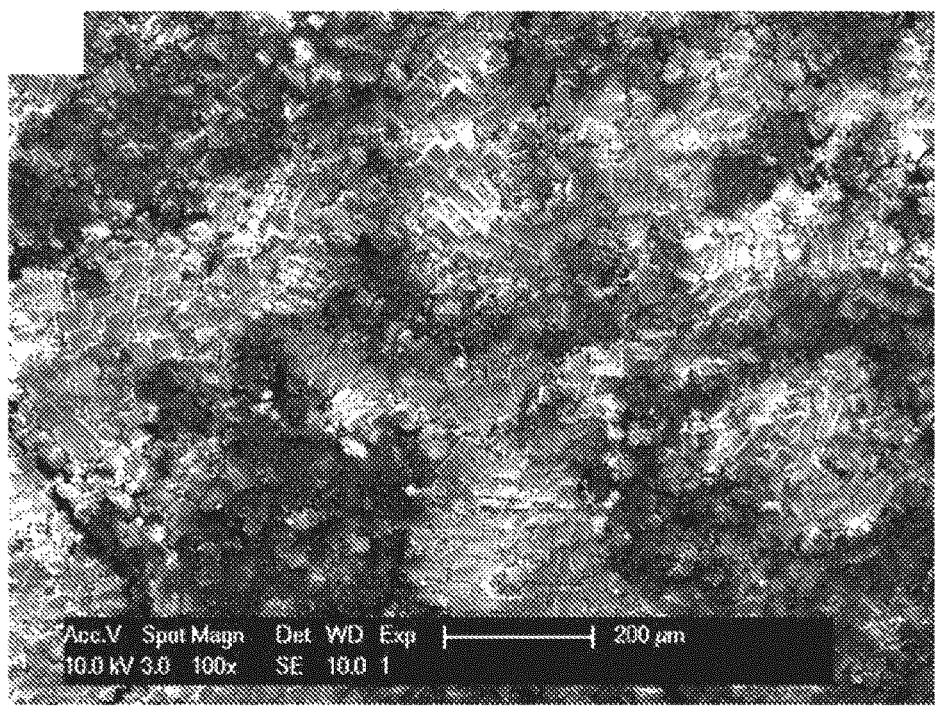
FIG. 6A is a light microscopy image of the unsintered green body after compressing the mixture of FIG. 5 at about 17,000 lbf, with a measurement bar identified as 200 µm, according to an exemplary embodiment of the present disclosure.
Figure 6B:
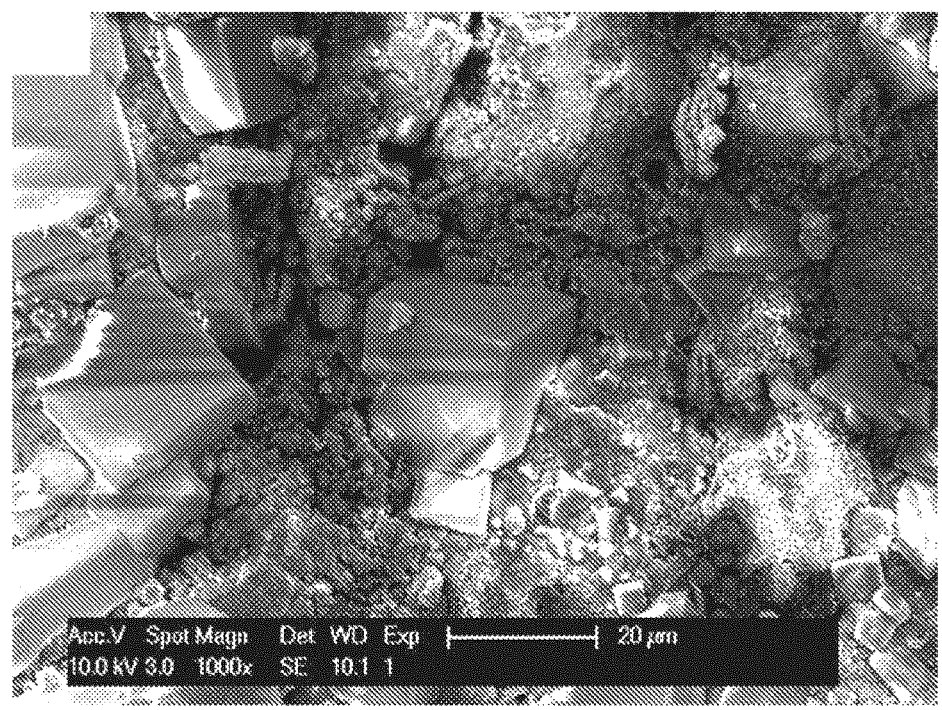
FIG. 6B is a light microscopy image of the unsintered green body after compressing the mixture of FIG. 5 at about 17,000 lbf, with a measurement bar identified as 20 µm, according to an exemplary embodiment of the present disclosure.
Figure 7:
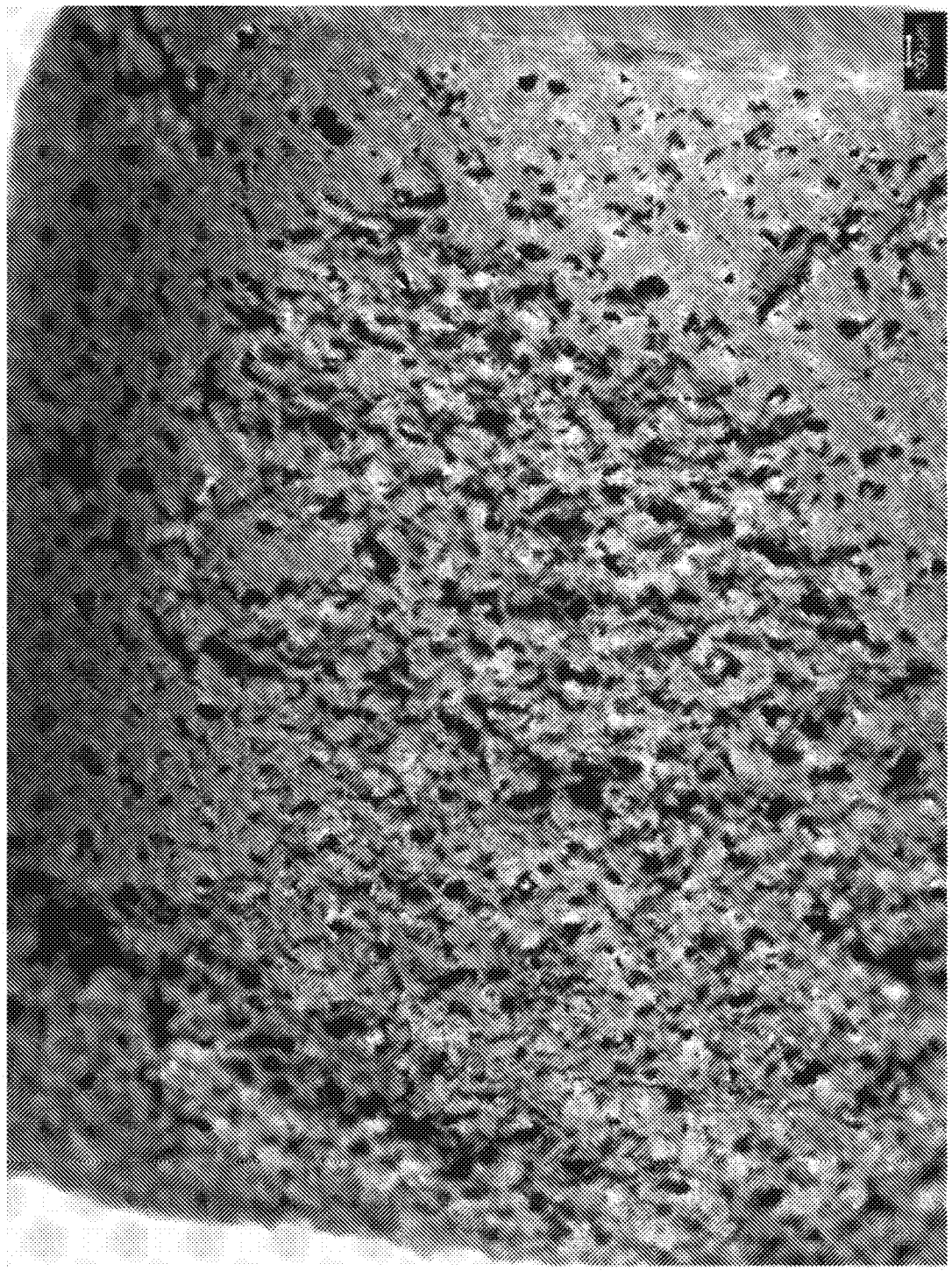
FIG. 7 is a light microscopy image after compressing the mixture of FIG. 5 at about 17,000 lbf, sintered at about 750° C. at about 10° C./min in flowing Argon for about 3 hours, washed with deionized water, and dried, according to an exemplary embodiment of the present disclosure.

Referring to FIGS. 6A and 6B, SEM images are shown after compressing the Fe—Mn-HA-NaCl mixture at about 17,000 lbf. FIG. 7 is a light microscopy image after compressing the mixture of FIG. 5 at about 17,000 lbf, sintered at about 750° C. at about 10° C./min in flowing Argon for about 3 hours, washed with deionized water, and dried. Referring to FIG. 7, an SEM image is provided depicting the first sintering followed by the dissolution process discussed herein. Pressures achieved during an example sintering process of the present disclosure achieved 600 MPa, converting to approximately 87,023 psi. In view of the foregoing, exemplary sintering pressures of the present disclosure can be referred to as about 17,000 lbf, 600 MPa, or other pressures useful to achieve the sintering process as referenced herein. In at least one example, and for a given setup and general diameter of sample created, a force of 17,000 lbf was achieved during the sintering process.

Figure 8A:
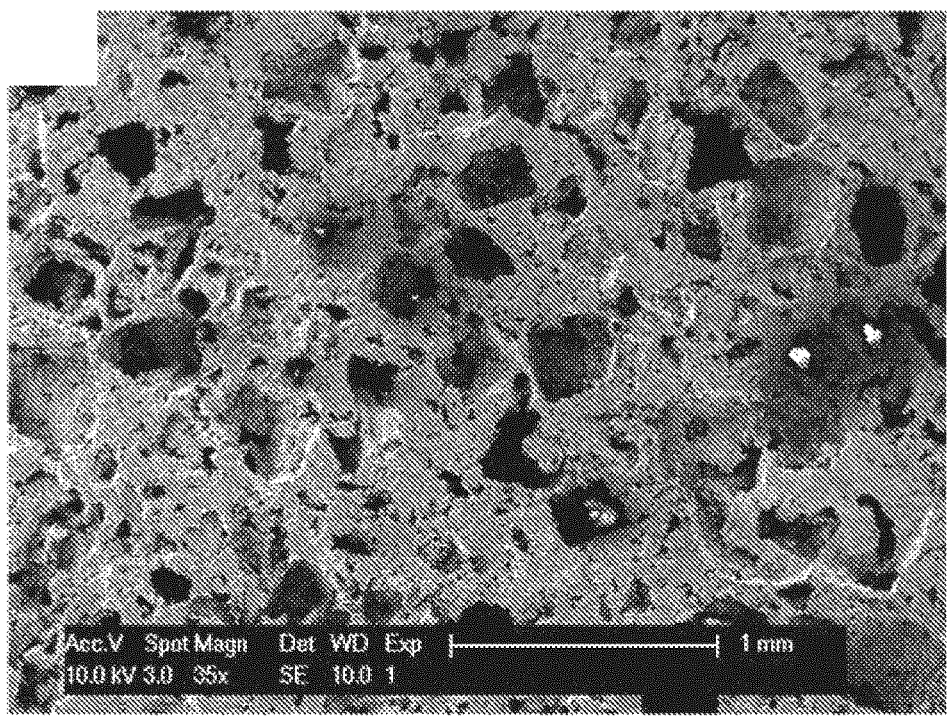
FIGS. 8A and 8B are SEM images depicting the first sintering and dissolution process discussed in FIG. 7, and sintered again at about 1200° C. at 10° C./min for about 3 hours, according to exemplary embodiments of the present disclosure.
Figure 8B:
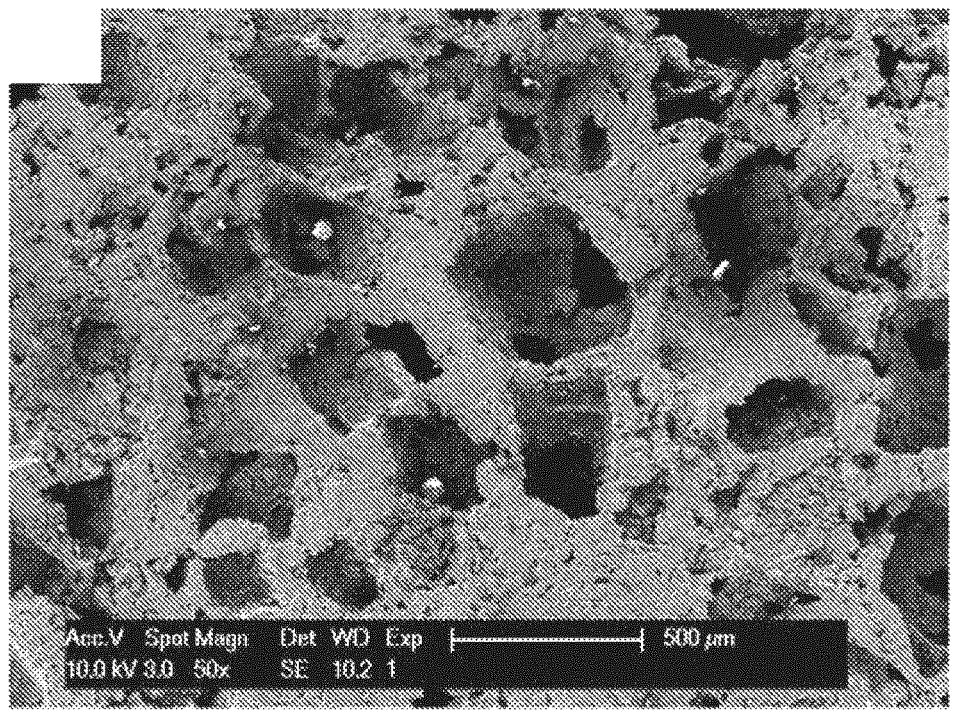
Figure 8C:
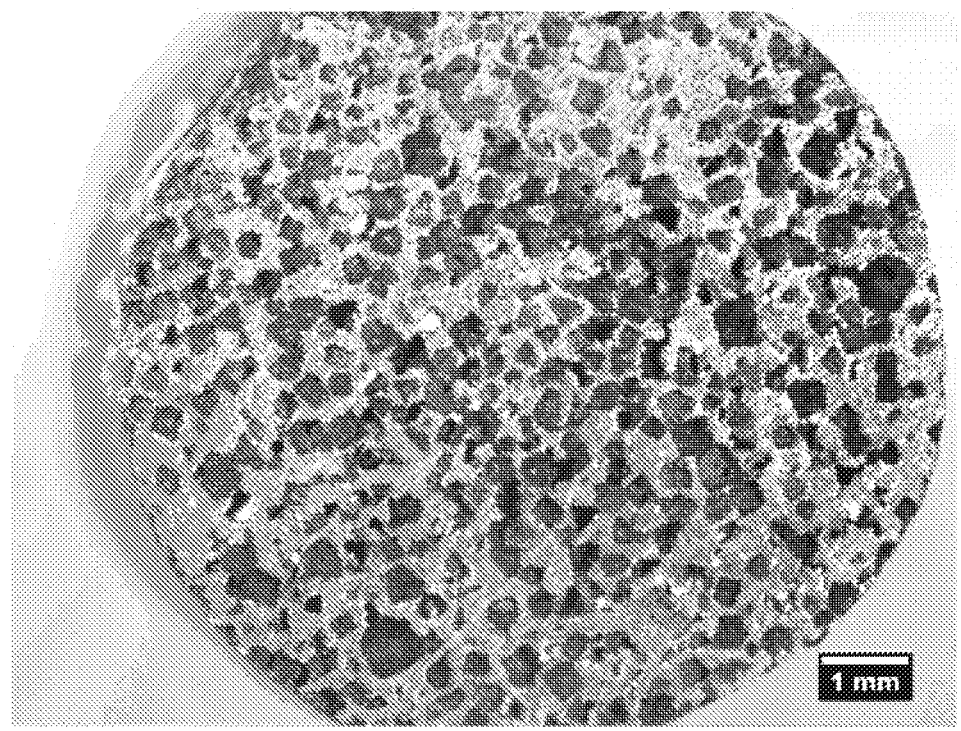
FIGS. 8C and 8D are light microscopy images depicting the first sintering and dissolution process discussed in FIG. 7, and sintered again at about 1200° C. at 10° C./min for about 3 hours, according to exemplary embodiments of the present disclosure.
Figure 8D:
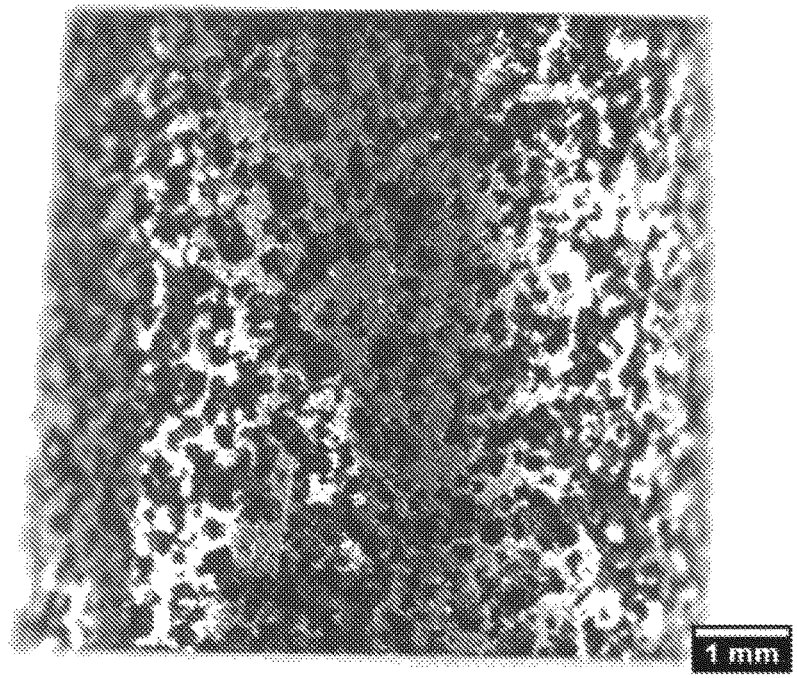
Figure 9A:
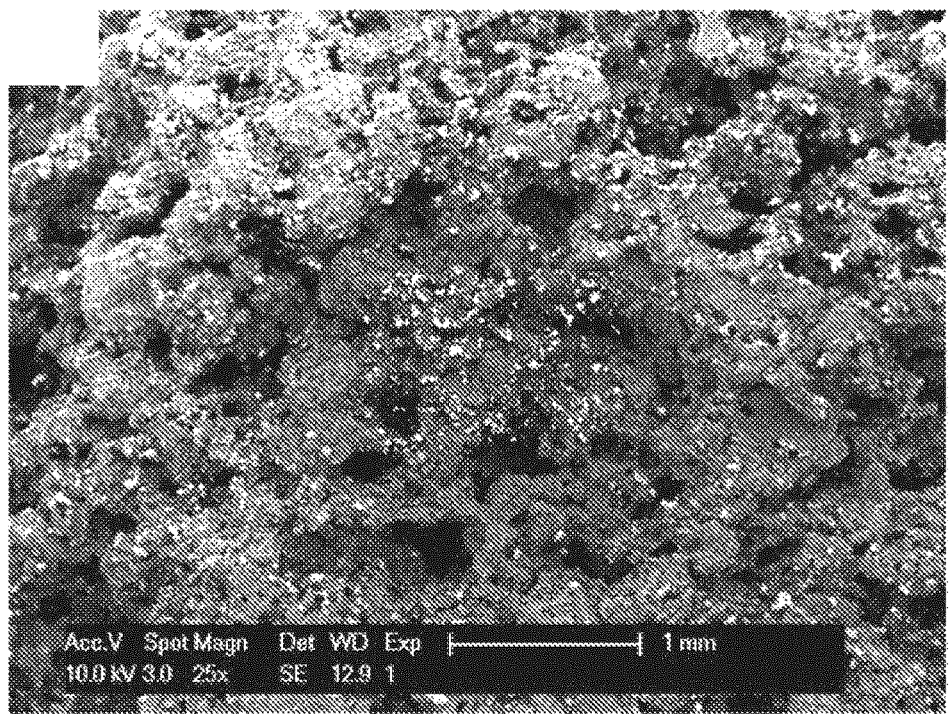
FIGS. 9A, 9B, 9C, and 9D are additional SEM images depicting the second sintering shown in FIG. 7 and a further dissolution process, further depicting the porosity on the surface based on % weight of NaCl, size and shape of powders and particles, sintering temperature, and sintering time, according to exemplary embodiments of the present disclosure.
Figure 9B:
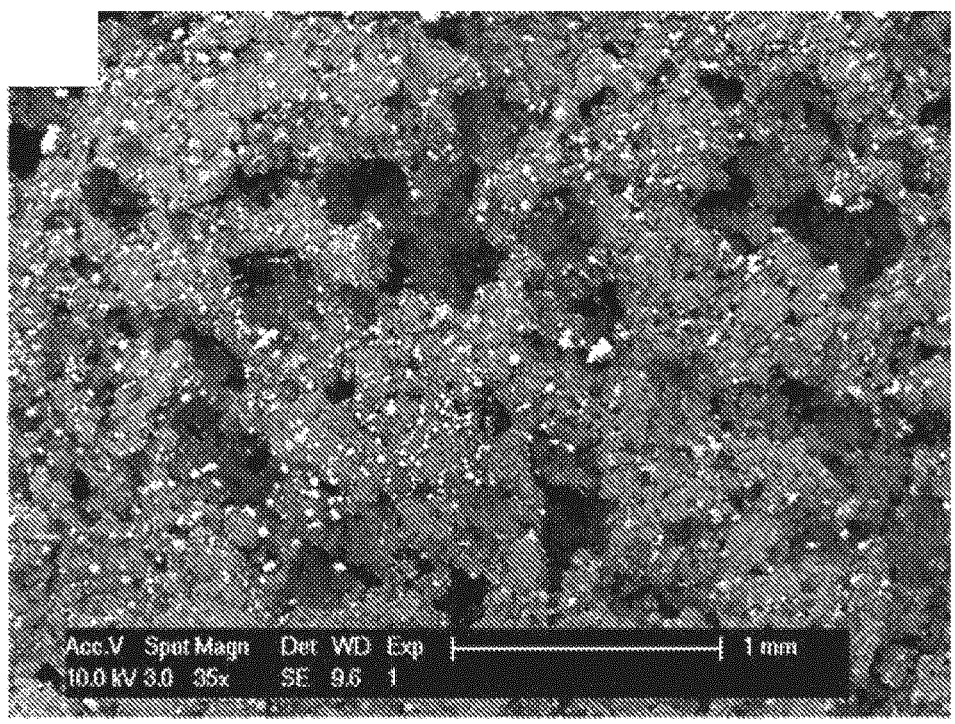
Figure 9C:
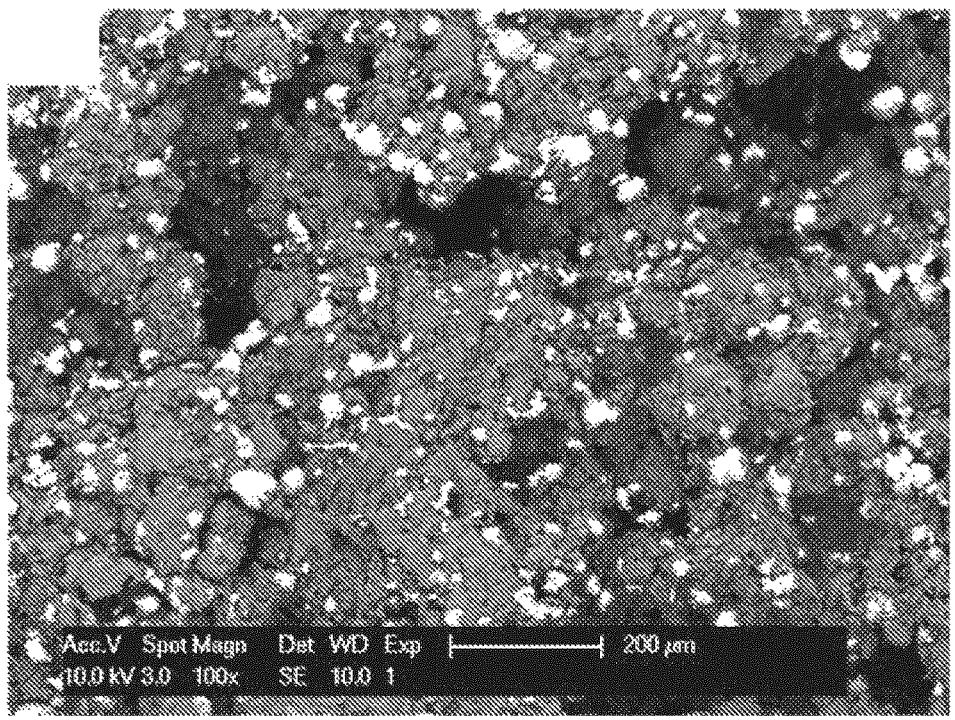
Figure 9D:
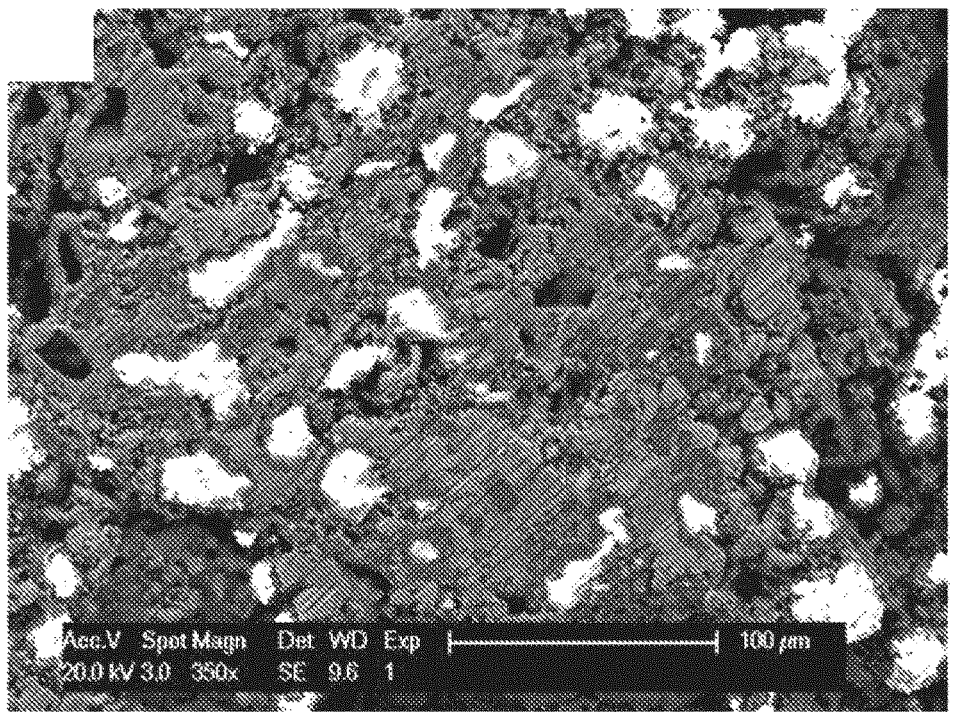
Figure 10A:
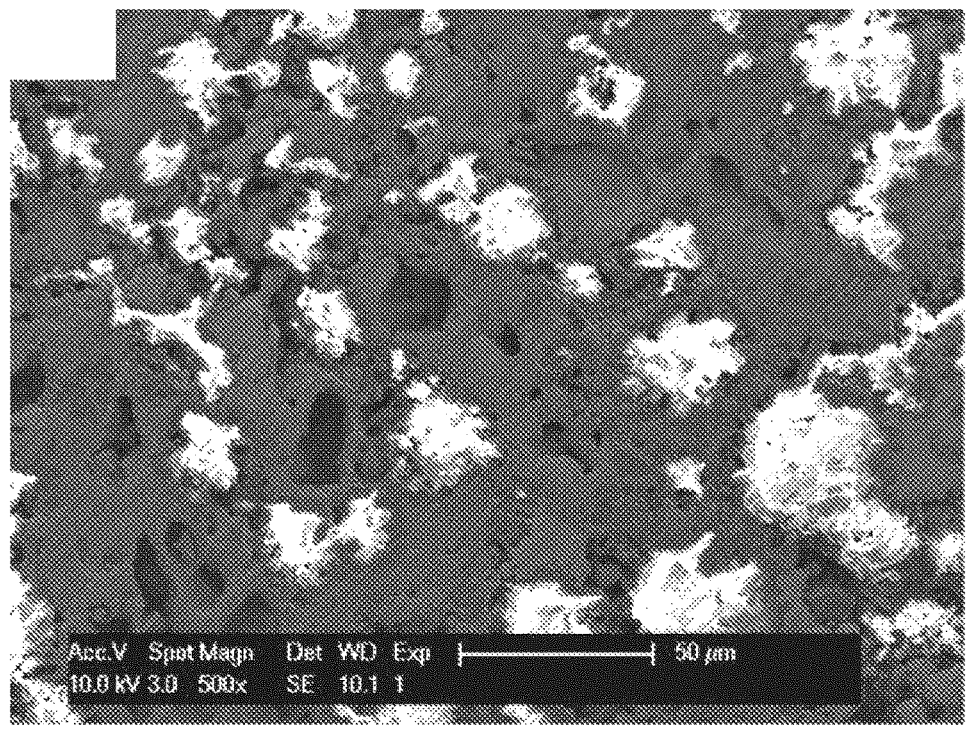
FIGS. 10A, 10B, 10C, and 10D are SEM images of FIGS. 9A, 9B, 9C, and 9D further magnified, according to exemplary embodiments of the present disclosure.
Figure 10B:
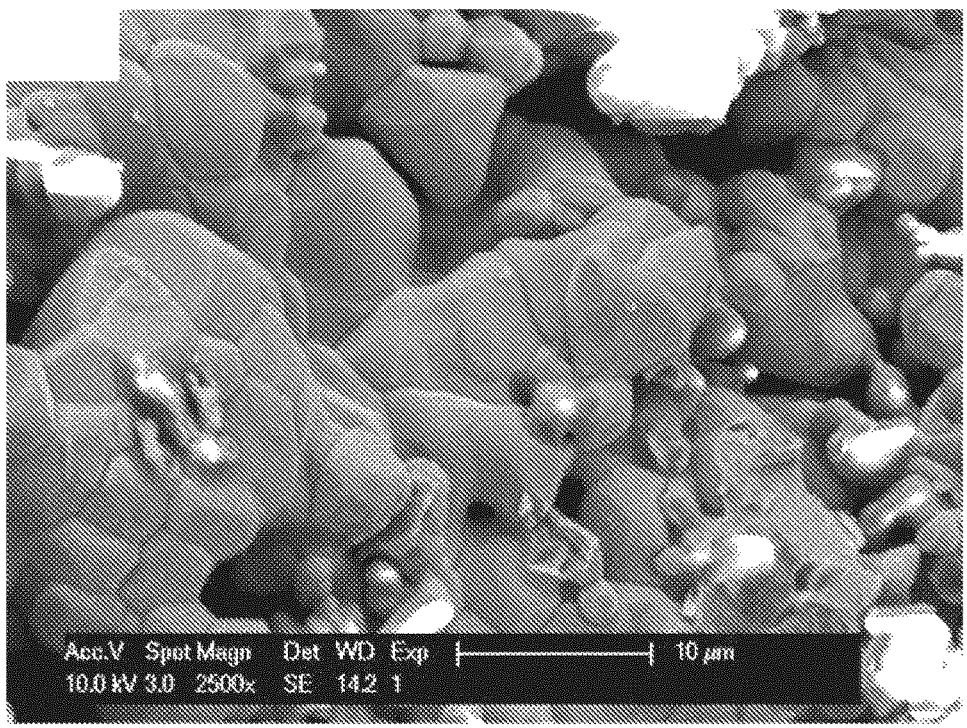
Figure 10C:
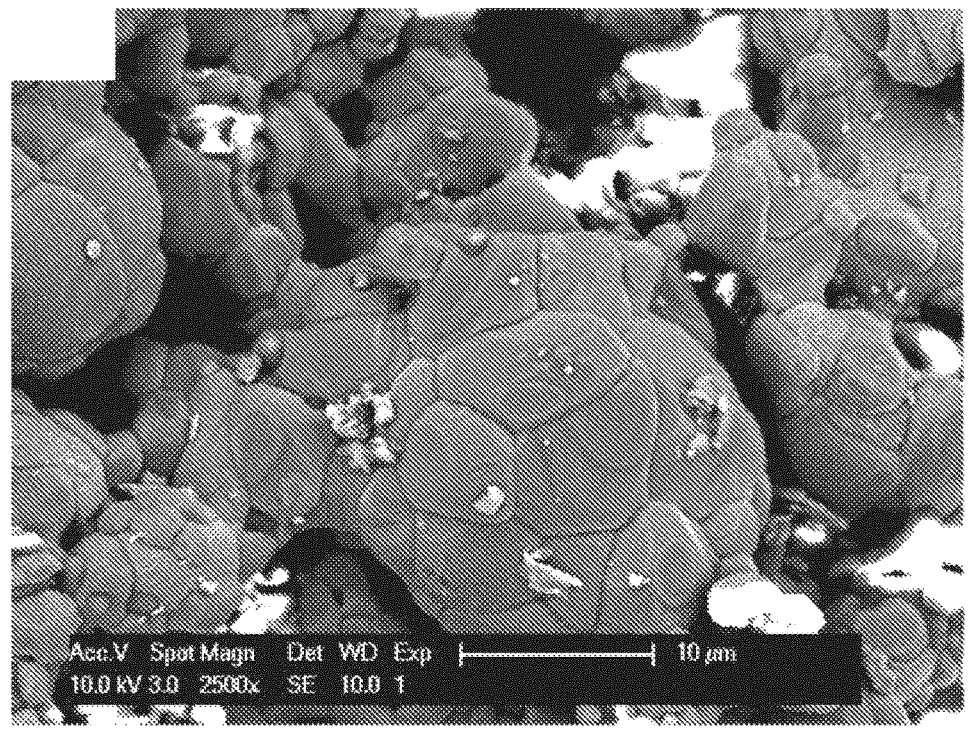
Figure 10D:
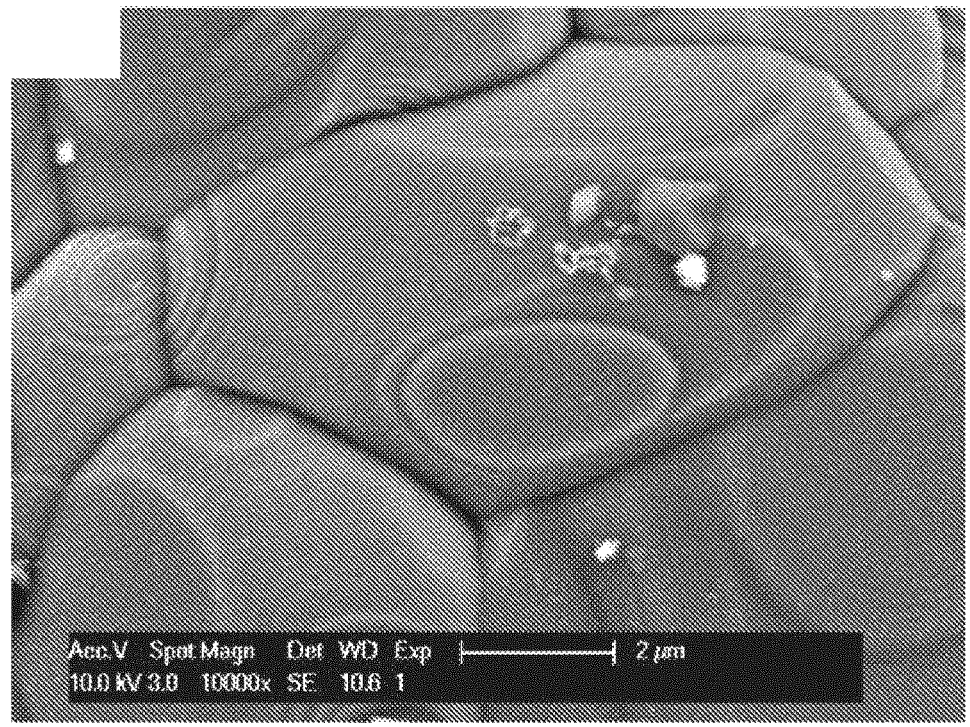

Referring to FIGS. 8A-8D, 9A-9D, and FIG. 10 as a further magnified version), SEM and/or light microscopy images after compressing the Fe—Mn-HA-NaCl mixture at about 17,000 lbf, sintered at about 750° C. at about 10° C./min in flowing Argon for about 3 hours, washed with deionized water to remove the salt, and sintered again at about 1200° C. at 10° C./min for about 3 hours, are shown therein. FIGS. 8A and 8B are SEM images, and FIGS. 8C-8D are light microscopy images depicting the first sintering and dissolution process discussed in FIG. 7, and sintered again at about 1200° C. at 10° C./min for about 3 hours (a second sintering). The measurement bars in each image are 1 μm. FIGS. 9A-9D are additional SEM images depicting the second sintering shown in FIG. 7 and a further dissolution process, further depicting the porosity on the surface based on % weight of NaCl, size and shape of powders and particles, sintering temperature, and sintering time. The measurement bars of FIGS. 9A and 9B are 1 μm, and the measurement bars of FIGS. 9C and 9D are 200 μm and 100 μm, respectively. FIGS. 10A-10D are further magnifications of aspects of FIGS. 9A-9D, whereby the measurement bars shown therein are 50 μm, 10 μm, 10 μm, and 2 μm within FIGS. 9A, 9B, 9C, and 9D, respectively.

Figure 11:
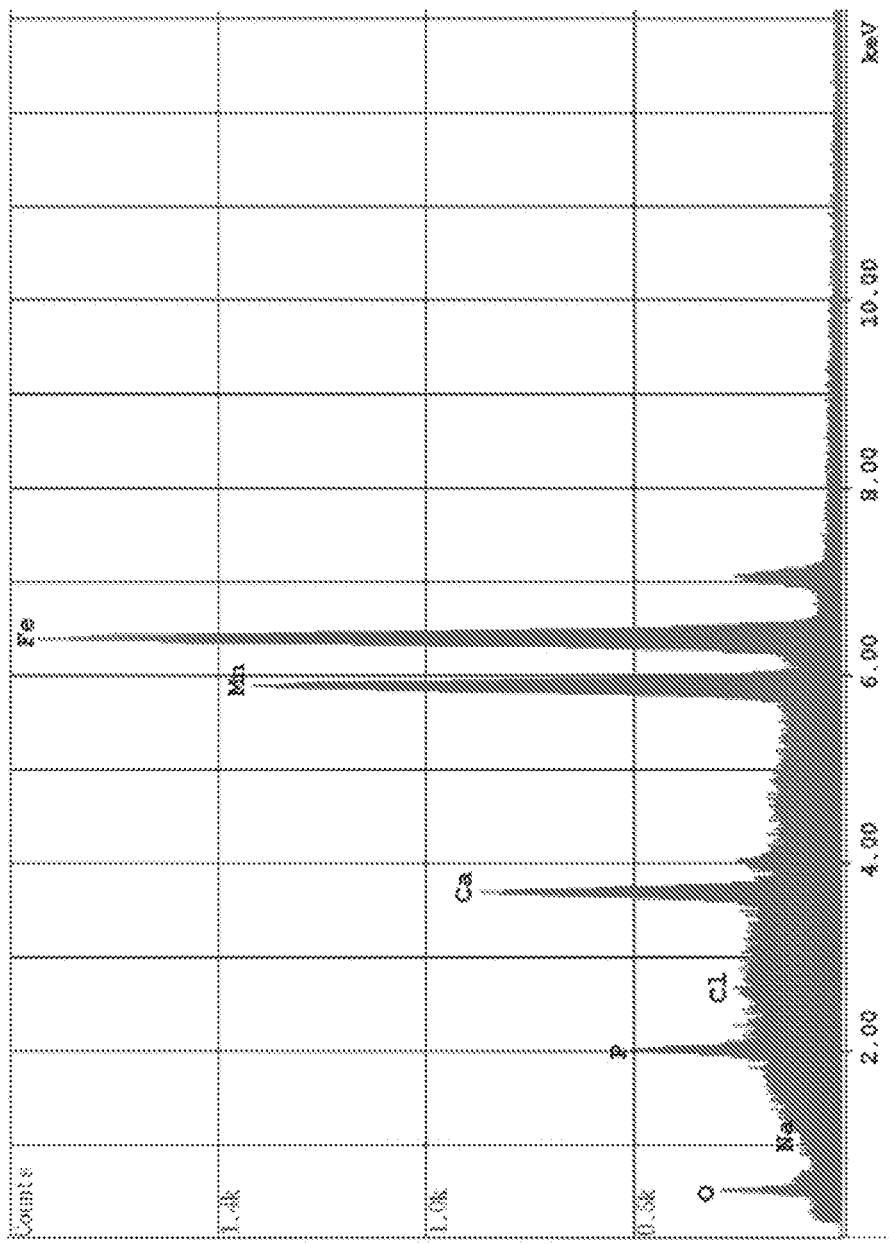
FIG. 11 is an output of Energy Dispersive X-ray Spectroscopy (EDS) in SEM identifying the elements present in the final processed composition and percent of each by weight, according to an exemplary embodiment of the present disclosure.

FIG. 11 is an output of Energy Dispersive X-ray Spectroscopy (EDS) identifying the elements present in the processed composition and percent of each by weight.

The process described above results in an implant product or material (referred to herein as an implant 100) having a porous surface having a first plurality of interconnected holes with a first range of sizes of, for example, at or between about 200 μm to about 1000 μm. Implant 100 therefore refers to the combination of metals, with an optional bone growth material, as referenced herein prior to molding/formation or as molded/formed to be a final implant or a portion thereof. The process described above can be further combined with a mold shape and/or a machining process resulting in a second plurality of interconnected holes having a second range of sizes that is at least about one order of magnitude larger than the first range of sizes, wherein the first plurality of holes being interconnected with the second plurality of holes. In addition to these interconnected secondary holes having sizes of an order of magnitude larger than the initial holes, smaller holes on the order of few nm can also be created from a dealloying process (such as by, for example, immersing in 5 wt % HCl for a variable amount of hours). The process described above results in another plurality of interconnected holes having another range of sizes that is at least about one order of magnitude smaller than the first range of sizes, wherein the first plurality of holes being interconnected with these plurality of holes. The surface of an implant 100 produced by the above-described process can comprise a surface roughness having between 2 nm and 5 μm of roughness. The roughness can be further promoted by a dealloying process that, e.g., etching the samples with 5 wt % HCl for 1-4 hours and heat treating said samples at 600° C. for 1 hour, thereby further promoting roughness. The bone growth material, as described above can be mixed into the Fe—Mn—NaCl mixture and sintered together; in which case, the bone growth material is integrated substantially equally into the implant 100. Alternatively, the bone growth material can be impregnated into a predetermined percentage of the interconnected holes in a post processing manner.

Figure 12:
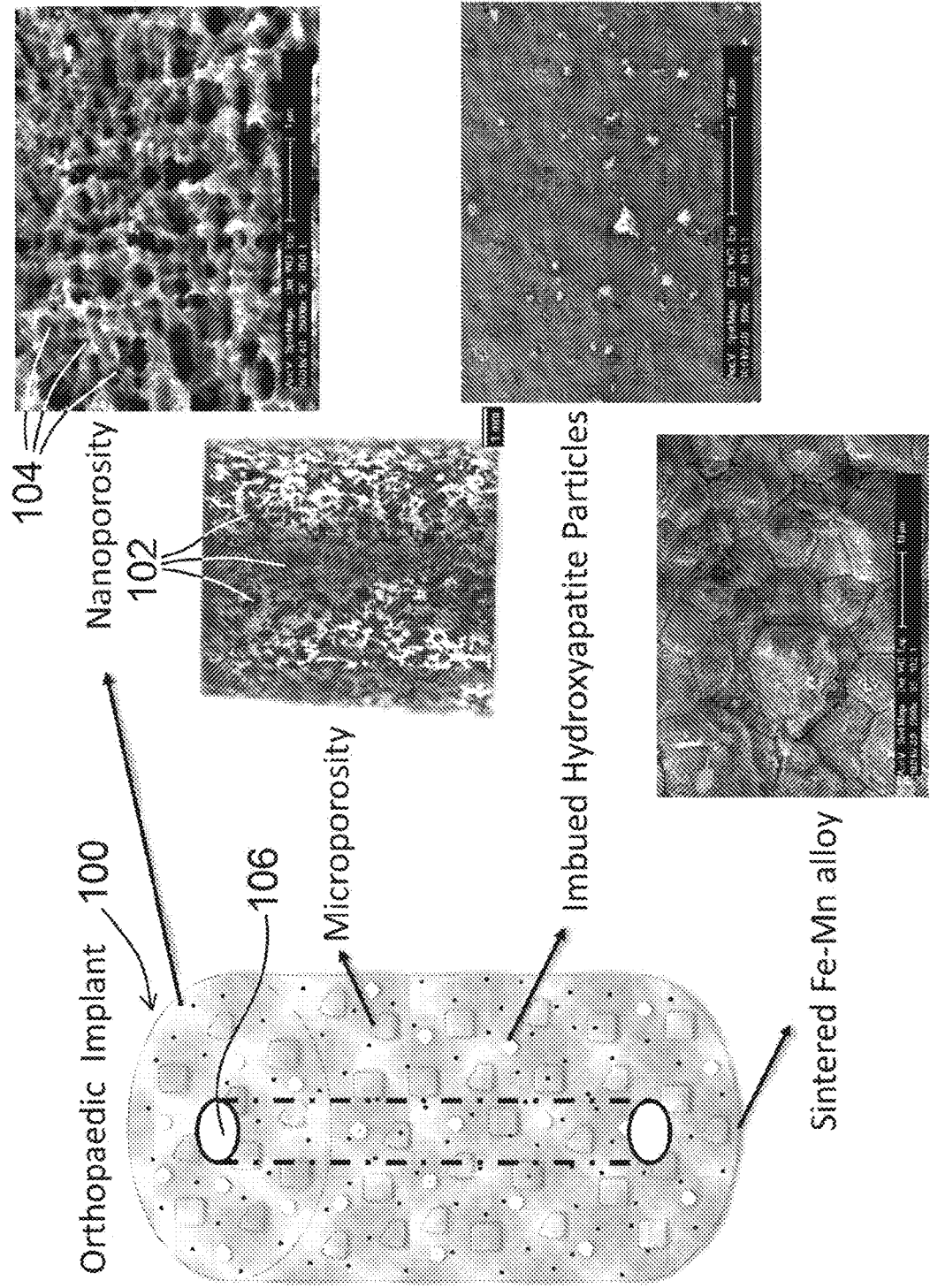
FIG. 12 is an image of an implant with photographs of various aspects of said implant at differing magnifications shown therein, according to an exemplary embodiment of the present disclosure.

An exemplary implant 100 of the present disclosure, as shown in FIG. 12, is generated by, and therefore includes, at least two metals (referred to herein as a first metal and a second metal). Said metals, in at least one embodiment, can comprise manganese and iron. The manganese and iron can be combined and sintered together, such as by heating the manganese and iron to an elevated temperature but below the melting point of the manganese (which is 1,246° C.) and the iron (which is 1,538° C.). For example, the first metal and the second metal can be sintered together at a temperature of at or about 750° C. or a higher temperature. In various embodiments, the sintering occurs at or between 750° C. and below 1,246° C., which is the melting point of the lower melting point metal (manganese).

FIG. 12 depicts an exemplary implant 100 of the present disclosure, and also shows various images to depict nanoporosity, microporosity, the bone growth material (such as hydroxyapatite) imbued within the implant 100, and the sintered alloy of two metals. The microporosity image shown in FIG. 12 includes a measurement bar identified as 1 mm, with a plurality of interconnected holes 102 defined therethrough. Said plurality of interconnected holes 102 can have a first range of pore sizes (opening diameters or general openings) between about 200 μm to about 1000 μm, as referenced herein. A dealloying process (such as by using acid, as referenced herein), can not only generate a surface roughness of at or between 2 nm and 5 μm, as referenced herein, but can also generate the second plurality of interconnected holes, having a smaller range of pore sizes (opening diameters or general openings) between about 10 nm to about 100 nm or generally smaller than 1 μm, which is at least one order of magnitude smaller than the first plurality of interconnected holes, if not more. For example, comparing 200 μm-1000 μm to 10 nm-100 nm, the difference is 3-4 orders of magnitude. The smaller plurality of interconnected holes 104 is depicted in the nanoporosity image shown in FIG. 12, including a measurement bar identified as 1 μm.

Sintering the first metal and the second metal together would generally result in a product that does not have any or an appreciable number of holes/openings/apertures defined therein. So to generate a plurality of interconnected holes, so to provide a place for actual bone or other material to grow therein upon implantation into a patient, the sintering can be performed by also mixing a salt, such as sodium chloride or another applicable salt, with the two metals. For example, a mixture of manganese, iron, and sodium chloride can be compressed at an elevated pressure (such as at our about 17,000 lbf or lower or higher) and at an elevated temperature (as referenced herein, noting that sodium chloride has a melting point of 801° C., so ideally the elevated temperature would be below 801° C. when using sodium chloride as the salt), whereby the sintering process is performed by increasing the temperature by a desired amount (such as 10° C./minute or a different rate) until the desired elevated temperature or elevated temperature range is met. This process can also be performed in the presence of a flowing noble gas, such as argon (Ar), and its duration can be for a desired amount of time, such as at or about 3 hours or more or less). After a desired amount of time, the sintered mixture can be cooled, and rinsed/washed, such as with water (such as deionized water), and ultimately dried or allowed to dry to form the implant material 100. The rinsing/washing step is performed to wash the mixture to rinse away the salt, as the salt is present throughout the sintered mixture, occupying physical space therein, until it is rinsed away using water or another liquid, for example. There may be instances whereby pockets within the sintered mixture contain sodium chloride that cannot be rinsed away, but in general, and as shown in FIGS. 9A-9D for example, a series of interconnected holes results from and corresponds to the physical space occupied by the sodium chloride or other salt prior to being rinsed away.

So to further promote bone growth when using said implant 100, a bone growth agent, such as hydroxyapatite, can be part of the mixture of the first metal, the second metal, and the salt. The same or similar heating, sintering, cooling, and washing/rinsing steps can be performed with the bone growth agent being part of the mixture. The bone growth agent therefore remains as part of the implant 100, and upon implantation of implant 100 into bone, the bone growth agent facilitates bone growth at a higher rate than would otherwise be facilitated without the use of the bone growth agent.

In view of the foregoing, the present disclosure includes disclosure of a sintered mixture comprising a first metal and a second metal, sintered in the presence of a salt. The salt can be rinsed away, if desired, to form a series of interconnected holes, also referred to as pores, openings, or channels, within the sintered mixture. A bone growth agent can also be part of the sintered mixture. The sintered mixture can also be shaped (cut, milled, etc.) to form a desired implant 100 shape/configuration. Exemplary implants 100 of the present disclosure can include, but are not limited to, pins, screws, anchors, plates, intervertebral fusion cages, rods, and/or components of hip or knee implants. As shown in FIG. 12, for example, an exemplary implant 100 can have a channel 106 defined therethrough, extending from one relative end/side of said implant 100 to another relative end/side of said implant. Said channel 106 can be sized and shaped to receive, for example, a metal, plastic, or other object or fluid therethrough when implant 100 is positioned within a body, for example.

An implant 100 generated by the above-referenced process will not have the typical issues of flaking in the resorption process that is experienced with other bioresorbable implants. Instead, the bioresorbable implant 100 of the present disclosure is configured to resorb into the body at substantially an atomic level without flaking off. The bioresorbable implant 100 of the present disclosure provide sufficient strength to fully support surrounding tissue during the natural healing period, provide biocompatibility without toxicity and inflammatory side effects, promote tissue generation on and about the implant, be compatible with magnetic environment, e.g., magnetic resonance imaging, and avoid release in the form of flaking of material beyond the body's natural systems are able to take up the released material.

While various embodiments of bioresorbable porous biocomposites for orthopaedic applications and methods of producing and using the same have been described in considerable detail herein, the embodiments are merely offered as non-limiting examples of the disclosure described herein. It will therefore be understood that various changes and modifications may be made, and equivalents may be substituted for elements thereof, without departing from the scope of the present disclosure. The present disclosure is not intended to be exhaustive or limiting with respect to the content thereof.

Further, in describing representative embodiments, the present disclosure may have presented a method and/or a process as a particular sequence of steps. However, to the extent that the method or process does not rely on the particular order of steps set forth therein, the method or process should not be limited to the particular sequence of steps described, as other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

The invention claimed is:

1. A method for producing a resorbable orthopaedic implant, comprising:
   generating a complex by compacting a quantity of a first metal, a second metal, and salt particles having a first range of sizes;
   sintering the complex at a first temperature below the melting point of the first metal, the second metal, and the salt particles;
   cooling the sintered complex to a second temperature below the first temperature; and
   washing the cooled sintered complex with a washing solution configured to wash away the salt particles so to generate a plurality of interconnected holes within an alloy core of the cooled complex that correspond to the first range of sizes of the salt particles.

2. The method of claim 1, further comprising the step of:
   dealloying the complex using an acid to provide a surface roughness between 2 nm and 5 μm and to generate a second plurality of interconnected holes smaller than the first range of sizes of the plurality of interconnected holes.

3. The method of claim 1, wherein the complex further comprises a bone growth agent, and wherein the bone growth agent remains as part of the complex after washing.

4. The method of claim 3, wherein the step of generating the complex comprises compacting the first metal comprising manganese (Mn), the second metal comprising iron (Fe), the salt particles comprising sodium chloride (NaCl), and the bone growth agent comprising hydroxyapatite (HA).

5. The method of claim 4, wherein the HA has an average diameter of about 24 μm.

6. The method of claim 1, wherein the step of compacting is performed at or about 17,000 lbf, and wherein the step of sintering is performed at or about 750° C.

7. The method of claim 1, wherein the sintering step comprises sintering the complex together in the presence of a flowing noble gas.

8. A method for producing a resorbable orthopaedic implant, comprising:
   generating a complex by compacting a quantity of a first metal, a second metal, a bone growth agent, and salt particles having a first range of sizes;
   sintering the complex together at a first temperature in the absence of oxygen, the first temperature below the melting point of the salt particles and the absence of oxygen achieved by the presence of a flowing noble gas;
   cooling the sintered complex to a second temperature below the first temperature; and
   washing the cooled sintered complex with a washing solution configured to wash away the salt particles so to generate a plurality of interconnected holes corresponding to the first range of sizes of the salt particles, and wherein the bone growth agent remains as part of the complex after the washing step.

9. The method of claim 8, wherein the first temperature is below the melting point of the first metal and the melting point of the second metal.

10. The method of claim 8, wherein the bone growth agent is hydroxyapatite (HA).

11. The method of claim 10, wherein the HA has an average diameter of about 24 μm.

12. The method of claim 8, wherein the first metal comprises manganese (Mn), the second metal comprises iron (Fe), and a ratio of Mn to Fe is at or about 25% Mn/75% Fe to at or about 40% Mn/60% Fe.

13. The method of claim 8, wherein the step of sintering the complex together at a first temperature is performed in the presence of flowing argon.

14. A method for producing a resorbable orthopaedic implant, the method comprising the steps of:
   sintering a complex at a first temperature in the presence of a flowing noble gas, the complex comprising a first metal, a second metal, and salt particles;
   washing the sintered complex with a washing solution to wash away the salt particles so to generate a plurality of interconnected holes corresponding to the salt particles; and
   sintering the washed sintered complex at a second temperature that is higher than the first temperature.

15. The method of claim 14, wherein the complex further comprises a bone growth agent that is sintered together with the first and second metals, wherein the bone growth agent remains as part of the complex after the washing step.

16. The method of claim 14, further comprising dealloying the sintered complex to generate a surface roughness at or between 2 nm and 5 μm.

17. The method of claim 14, wherein the salt particles have a range of sizes and the plurality of interconnected holes within the sintered complex have sizes corresponding to the range of sizes of the salt particles.

18. The method of claim 14, wherein the first metal comprises manganese, the second metal comprises iron, the salt particles comprise sodium chloride, and the bone growth agent comprises hydroxyapatite.

19. The method of claim 14, wherein the first temperature is a temperature below a melting point of the salt particles.

20. The method of claim 14, wherein the first temperature is at or about 750° C. and the second temperature is at or about 1200° C.

* * * * *